United States Patent [19]

Philipp

[11] Patent Number: 5,093,593
[45] Date of Patent: Mar. 3, 1992

[54] SURGICAL HANDPIECE WITH MOTOR HAVING POSITIVE SENSOR LOCATION

[75] Inventor: Christopher D. Philipp, Kalamazoo, Mich.

[73] Assignee: Stryker Corporation, Kalamazoo, Mich.

[21] Appl. No.: 629,234

[22] Filed: Dec. 18, 1990

[51] Int. Cl.⁵ .................. H02K 3/26; H02K 37/04; H02K 7/14
[52] U.S. Cl. ............................ 310/71; 310/47; 439/65
[58] Field of Search ............ 310/47, 50, 71, DIG. 6; 439/38, 45, 47, 65, 74, 75, 824

[56] References Cited

U.S. PATENT DOCUMENTS

| | | | |
|---|---|---|---|
| 2,993,391 | 7/1961 | Raney | 310/50 |
| 4,859,188 | 8/1989 | Neumann | 439/65 |
| 4,911,645 | 3/1990 | August et al. | 439/75 |
| 4,988,905 | 1/1991 | Tolmie, Jr. | 310/68 B |

Primary Examiner—Steven L. Stephan
Assistant Examiner—D. L. Rebsch
Attorney, Agent, or Firm—Flynn, Thiel, Boutell & Tanis

[57] ABSTRACT

A dc permanent magnet motor for a surgical handpiece, comprises a housing and a stator including windings fixed in the housing. A rotor is supported for rotation in the housing and has a forward extending rotatable shaft. A conventional sensor adjacent the windings and rotor has stiff conductive electrodes extending rearward. A printed circuit board disk has plural axial holes along the perimeter thereof defining conductive sockets into which the electrodes plug, which disk is located coaxially rearward of said rotor and windings and is fixed with respect to the housing. A rear-facing, separable connector holder behind the printed circuit board has terminals rear-facing therefrom for connection to an external electrical supply. The holder is fixed with respect to the housing. Electrical connections are effected between the conductive sockets of the printed circuit board and the rear-facing terminals of the holder.

15 Claims, 3 Drawing Sheets

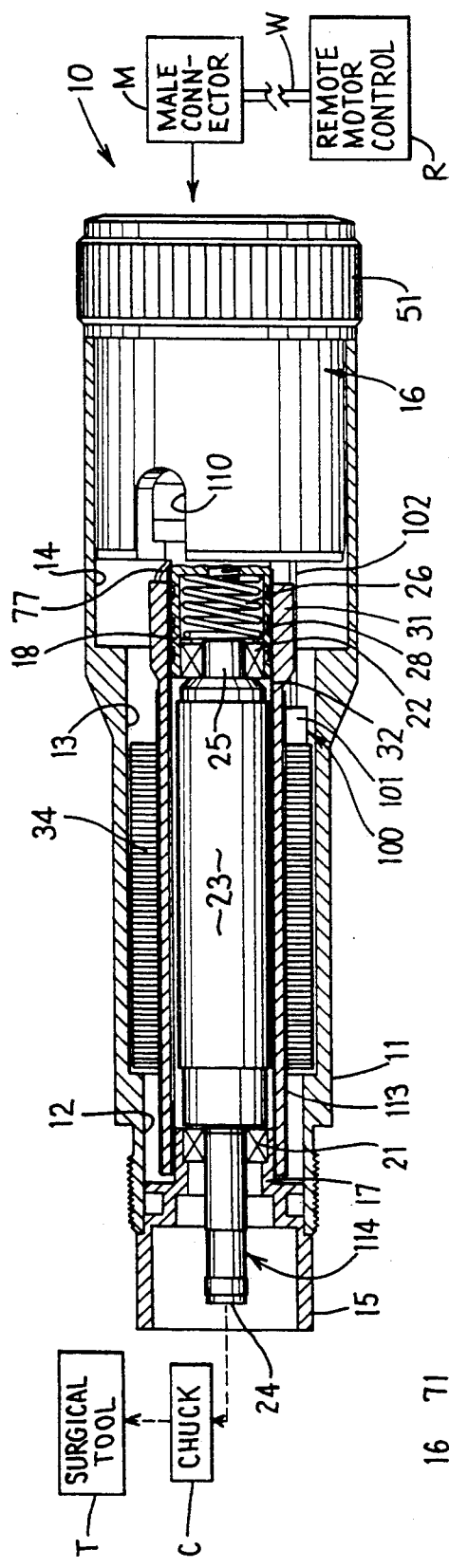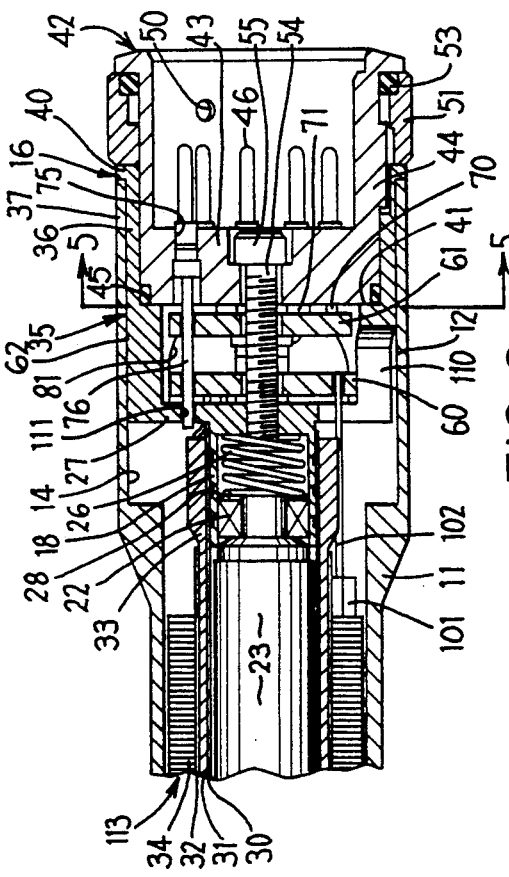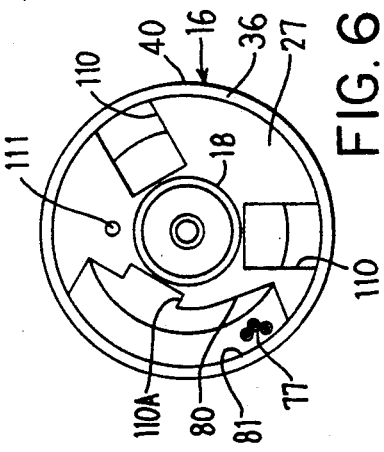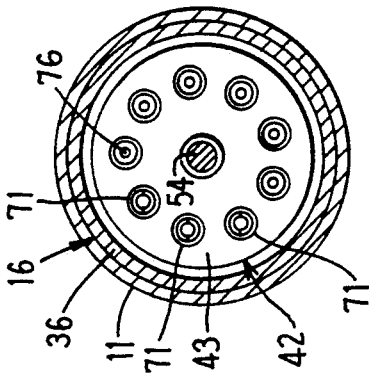

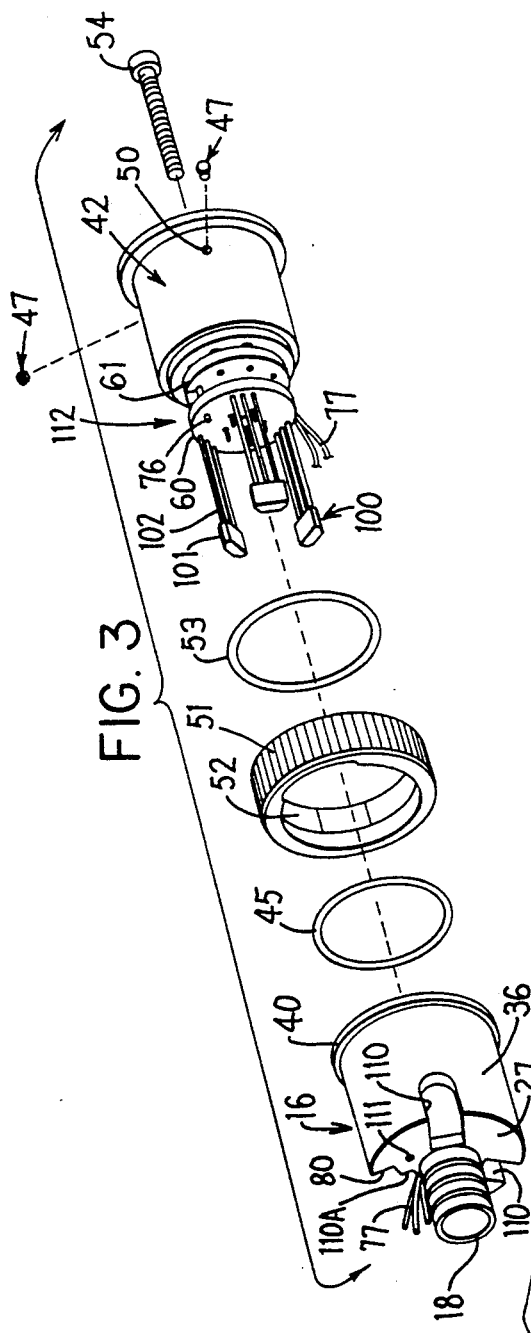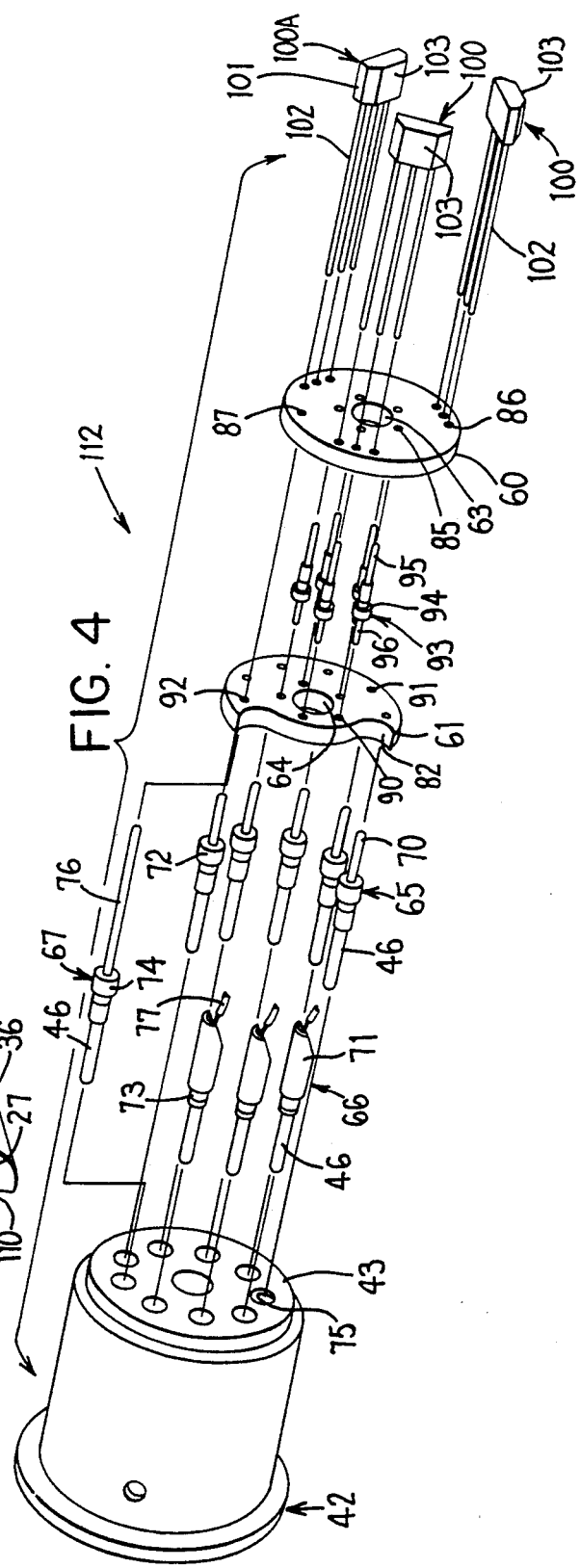

5,093,593

SURGICAL HANDPIECE WITH MOTOR HAVING POSITIVE SENSOR LOCATION

FIELD OF THE INVENTION

This invention relates to an electrically powered surgical handpiece of the type incorporating a compact, high-speed dc brushless motor having rotor position control sensors.

BACKGROUND OF THE INVENTION

In a prior surgical handpiece of the above-mentioned type, marketed by the assignee of the present invention, rotor position sensors, typically Hall sensors, are circumferentially spaced around one end portion of a permanent magnet rotor to continuously sense the circumferential location of the rotating magnetic poles of such rotor and thereby, through a suitable conventional control circuit, control polarity and amplitude of the energization of stator windings, to cause the handpiece to drive a surgical tool in the desired rotation direction and at the desired speed. Handpieces of this type incorporate high speed motors, for example in the range of 40,000 rpm to 100,000 rpm.

In this prior handpiece motor, elongate insulated wires are soldered to short trimmed conductive leads of the sensors and to stator field winding ends and are bent through a common tortuous path rearwardly to soldered connections on the front of a rear opening, cup shaped pin holder at the rear of the handpiece. Rear facing pins of the pin holder releasably engage sockets in a conventional plug insertable into the rear end of the handpiece. The plug connects through an elongate multiconductor cable to conventional control circuitry in a remote console. With three sensors and three pins per sensor, the result was nine elongate insulated sensor wires, in addition to three more field winding wires, led tortuously through the handpiece housing and 24 solder connections. Accordingly, the assembly of these parts was labor intensive and thus costly. There was risk of bad solder joints. In addition, the required length and flexibility of the tortuously led insulated connecting wires prevented these wires from themselves reliably positively locating the sensors precisely with respect to each other and the rotor. In addition, the bundle of the insulated connecting wires taken in total, was bulky and at odds with the need for compactness in a motor structure to be inserted into a comfortable handheld surgical handpiece. Further, this prior arrangement of insulated connecting wires risked pinching and breaking of individual wires and loosening of solder joints during assembly into the handpiece housing, requiring subsequent repair. Accordingly, the objects and purposes of the present invention include provision of a surgical handpiece of the type aforementioned, but having improved physical mounting and electrical connection structure for the sensors and which avoids the difficulties in the prior structure above-discussed.

Other objects and purposes of the invention will be apparent to those acquainted with the apparatus of this general kind upon reading the accompanying description and inspecting the accompanying drawings.

SUMMARY OF THE INVENTION

A dc permanent magnet motor for a surgical handpiece, comprises a housing and a stator including windings fixed in the housing. A rotor is supported for rotation in the housing and has a forward extending rotatable shaft. A conventional sensor adjacent to the windings and rotor has stiff conductive electrodes extending rearward. A printed circuit board disk has plural axial holes along the perimeter thereof defining conductive sockets into which the electrodes plug, which disk is located coaxially rearward of said rotor and windings and is fixed with respect to the housing. A rear facing, separable connector holder behind the printed circuit board has terminals rear-facing therefrom for connection to an external electrical supply. The holder is fixed with respect to the housing. Electrical connections are effected between the conductive sockets of the printed circuit board and the rear-facing terminals of the holder.

BRIEF DESCRIPTION OF THE DRAWINGS

FIG. 1 is a central cross-sectional view of a surgical handpiece incorporating dc powered motor with a permanent magnet rotor, and embodying the present invention.

FIG. 2 is a view similar to FIG. 1 with the rear bearing housing and pin holder broken away in central cross section.

FIG. 3 an exploded pictorial view, in reduced scale, of the pin holder and rear bearing housing, and additional elements associated with mounting of the sensors, of FIGS. 1 and 2.

FIG. 4 is an enlarged pictorial exploded view of elements directly associated with the pin holder of FIG. 3.

FIG. 5 is a central cross-sectional view substantially taken on the line 5–5 of FIG. 2.

FIG. 6 is an end view of the forward end of the rear bearing housing of FIGS. 1–3.

DETAILED DESCRIPTION

Figure 7:
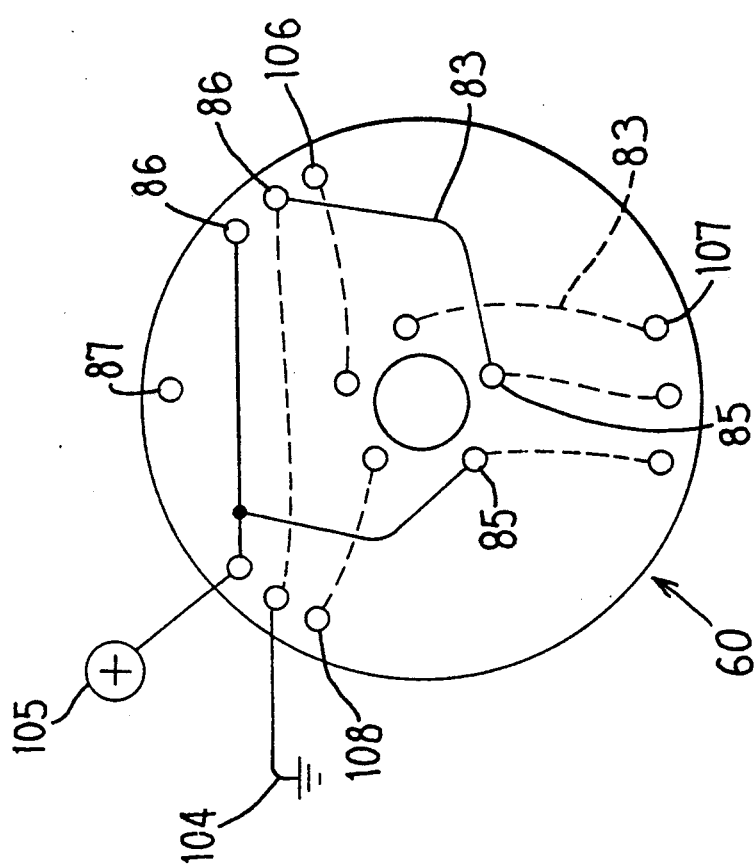
FIG. 7 is an enlarged front elevational view of a front (left) printed circuit board disk of FIG. 4.

FIG. 1 discloses a surgical handpiece 10 comprising an elongate hollow housing 11. The housing 11 has front, middle and rear chambers 12, 13 and 14 of internal diameter which steps up rearwardly. Hollow front and rear bearing supports 15 and 16 are telescoped fixedly in the front and rear ends, respectively, of the housing 11 and include respective, reduced diameter, inner end portions 17 and 18, respectively, formed as tubular necks, extending coaxially toward each other within the housing 11. Front and rear bearings, here low friction bearings, 21 and 22 are disposed in the adjacent inner ends of the reduced diameter necks 17 and 18, respectively. A permanent magnet rotor 23 is disposed loosely within the middle chamber 13 of the housing 11 and is carried rotatably and axially snugly between the front and rear bearings 21 and 22. Front and rear shaft ends 24 and 25 extend fixedly and coaxially forward and rearward from the rotor 23 and rotatably support the rotor on the front and rear bearings 21 and 22 respectively. The front bearing 21 is precisely axially fixed against forward movement by a rearward facing step in the rear extending neck 17 of the front bearing support 15 so as to positively and precisely locate the permanent magnet rotor 23 against forward movement with respect to the housing 11.

The annular neck 18 of the rear bearing support 16 is generally cup-shaped and contains a coil compression spring 26. The spring 26 is backed by the bottom, or rear radial wall, 27 of the cup-shaped neck 18 and, through a washer 28, urges the rear bearing 22 forward to thereby resiliently axially urge the permanent magnet rotor 23 against the fixedly backed front bearing 21, to precisely locate the permanent magnet rotor axially within the housing 11.

A thin but rigid dielectric sleeve 30 serves as a cylindrical coil form, on the outer face of which is wound the stator windings 31 (FIG. 2). The dielectric sleeve 30 and stator windings 31 surrounding same extend at their front and rear ends over the annular necks 17 and 18, respectively, of the front and rear bearing supports 15 and 16. The dielectric sleeve 30 is fixed, by any convenient means such as an adhesive, to the rear neck 18 and fits radially snugly over both necks 17 and 18 to fixedly locate same with respect thereto. The dielectric sleeve 30 is a coaxial, close-clearance fit around the rotatable rotor, which is freely rotatable therein. An outer dielectric sleeve 32 closely and fixedly surrounds the stator windings 31 except for the rearwardmost portion 33 thereof. An axial stack 34 of washer-like, magnetizable laminations is closely radially sleeved over and fixed with respect to the outer dielectric sleeve 32. The laminations stack 34 extends almost the length of the permanent magnet rotor 23. The laminations stack 34 is a close but axially slidable fit within the middle chamber 13 of the housing 11.

Thus, the laminations stack 34, dielectric sleeve 32, stator windings 31 and dielectric sleeve 30 are fixed on the necks 17 and 18 of the front and rear bearing supports 15 and 16, respectively, and serve as the stator of the motor and thus cooperate with the permanent magnets of the rotor 23 to cause rotation of the rotor 23 and shaft ends 24 and 25 in response to proper electrical energization of the windings 31.

A conventional chuck, or other tool mounting structure, schematically indicated at C (FIG. 1), is affixable to the front shaft end 24 in a conventional manner to carry and rotatably drive a conventional surgical tool, schematically indicated at T.

The rear bearing support 16 has an enlarged diameter, generally cylindrically cup-shaped rear body 35 (FIG. 2) which extends coaxially rearward from the bottom 27 of the neck 18 in an integral manner. Thus, the cup-shaped, oppositely facing neck 18 and body 35 share the bottom wall 27, which extends radially outward from the neck 18 substantially to the interior face of the rear chamber 14 of the housing 11. Indeed, the generally cylindrical side wall 36 of the body 35 is fixed, preferably by a press fit, axially in the rear chamber defining portion 37 of the body 35. A radially outward extending flange 40 fixed on the rear end of the body 35 positively stops forward movement of the body 35 into the housing 11 and thus positively axially locates the rear bearing support 16 in the housing 11.

The interior of the body cylindrical side wall 36 defines, generally axially centrally thereof, a rearward facing, radially inward extending step 41. A rearward opening, cup-shaped, pin holder 42, of suitable plastics material, has a relatively thick bottom wall 43 radially extending out to a substantially cylindrical side wall 44. The side wall 44 extends rearward from the bottom wall 43 beyond the rear end of the rear bearing support 16. The cup-shaped pin holder 42 is fixed, by a screw 54 hereafter discussed, within the rearward opening body 35, and the forward end of the bottom wall 43 abuts the step 41 to fixedly locate the pin holder 42 precisely in the rear bearing support 16.

An annular resilient seal 45, such as an O-ring, surrounds the front end portion of the pin holder 42 to seal against the step 41 in the rear portion of the side wall 36 of the rear bearing support 16, to prevent liquid leakage forwardly therebetween into the midportion of the interior of the housing 11.

Electrically conductive pins 46 are circumferentially spaced on and extend rearward from the bottom wall 43 of the pin holder 42. The pins 46 are arranged in a conventional pattern and the rearward opening interior of the cup-shaped pin holder 42 is conventionally sized to receive a conventional male connector schematically indicated at M (FIG. 1) having a corresponding circumferentially arranged and spaced array of pin receptacles (not shown) connected to a conventional multiwire cable schematically indicated at W leading to a conventional remote motor control schematically indicated at R.

A suitable conventional male connector M and cable W is available as a unit, namely the Model No. 296-4 available from the assignee of the present invention, namely Stryker Corporation, located at 420 Alcott Street, Kalamazoo, Mich. 49001. Similarly, a suitable conventional remote motor control R is available as the Model No. 296-1 from Stryker Corporation, located at 420 Alcott Street, Kalamazoo, Mich. 49001. In the embodiment shown, the cup-shaped pin holder 42 and the male connector M define an axially separable electrical connector of conventional type. More particularly, such conventional type is here shown as the type utilizing a headed button, or buttons 47, (see FIG. 3), each extending radially inward through a corresponding radial through hole 50 in the side wall 44 of the pin holder 42 to thereby engage the male connector M. To this end, a conventional cam ring 51 (FIGS. 1, 2 and 3) is provided with internal, circumferentially extending ramps 52 (FIG. 3) which slope radially along their circumferential lengths and are radially engagable with the outer ends of the buttons 47 to alternately (1) press them radially inward against the conventional male connector M or to (2) allow such buttons to be displaced radially outward to thereby (1) lock or (2) unlock the conventional male connector M with respect to the pin holder 42.

A relatively large cross section O-ring 53 is radially partially compressed between the cam ring 51 and the side wall 44 surrounded thereby, to frictionally resist unintended rotation of the cam ring 51 on the pin holder 42 but allow intended rotation thereof. In this way, rotation of the cam ring 51 actuates the buttons 47 radially inward to engage the male connector M and, alternatively, allows the buttons to shift radially outward to release such connector. As seen in FIG. 3, the buttons 47 have radially enlarged heads 57 of diameter larger than the holes 50 so as to maintain the buttons 47 captive with their heads 57 radially between the cam ring 51 and the side wall 44 of the pin holder 42.

Other types of conventional connector locking means may be substituted, if desired.

To the extent above-described, the apparatus is conventional.

Turning now more particularly to portions of the apparatus more directly concerned with the present invention, front and rear printed circuit (PC) boards 60 and 61 (FIGS. 2, 3 and 4) are disposed within the forward portion 62 of the body 35 of the rear bearing support 16 (FIG. 2), if desired with suitable coaxial spacers locating same in axially spaced relation from each other and between the bottom wall 27 of the rear bearing support 16 and the bottom wall 43 of the pin holder 42. The screw 54 is centrally threadedly received in the bottom wall 27 of the rear bearing support. The head 55 of the screw 54 bears forwardly on the bottom wall 43 of the pin holder 42. The circuit boards 60 and 61 have respective central bores 63 and 64 (FIG. 4) which loosely coaxially receive the screw 54. Tightening the screw 54 seats the pin holder 43 firmly forward against the step 41 of the rear bearing support 16.

In the embodiment shown, the rear facing pins 46 of the pin holder are integral rear portions of elongate conductive terminals 65, 66 and 67. The terminals 65 are here five in number, are identical, and each have forward extending pins 70 coaxial with the corresponding rearward extending pins 46 integral therewith. The terminals 66, here three in number, have forward extending female sockets 71. The terminals 65, 66 and 67 have respective enlarged diameter midportions 72, 73 and 74 which are fixed, by any convenient means in respective axial through holes 75 through the bottom wall 43 of the pin holder 42. Thus, the pins 46 extend rearwardly into the interior of the cup-shaped pin holder 42 as above described, and the pins 70 and 71 extend forward from the pin holder bottom wall 43. The terminal 67 is a ground terminal and has an extra long pin 76 extending forward therefrom for purposes appearing hereafter. The sockets 71 are relatively short so that they are flush with or extend only slightly forward from the front of the bottom wall 43 of the pin holder, whereas the pins 70 and 76 extend significantly beyond such bottom wall 43.

Insulated wires 77, here three in number, are the ends of the stator windings and are led rearward (FIGS. 1 and 2) from the rear end of the stator windings 31 through a circumferentially enlarged opening 80 (FIG. 6) in the bottom wall 27 of the rear bearing support 16. The three insulated wires 77 are thus led into the interior of the cup-shaped, rear opening body 35 of the rear bearing support 16 past the periphery of the front circuit board 60. To facilitate this, the opening 80 in the bottom 27 extends rearward into the forward portion 62 of the sidewall 36 of the rear bearing support 16, beyond the forward circuit board 60 and substantially to the rearward circuit board 61, to thereby form a forward opening notch 81 (FIGS. 2 and 6).

A relatively wide circumferential portion of the rear PC board disk 61 is omitted to form a sinuously curved, relatively wide circumferential notch 82 (FIG. 4) which is axially aligned with the notch 81 and opening 80 in the rear bearing support 16.

Accordingly, the insulated wires 77 are led from the rear end of the stator windings 31 rearward through the opening and notch 81 into the interior of the rear bearing support, past the front and rear PC board disks 60 and 61, and particularly through the notch 82 in the latter. The bared rear ends of the insulated wires 77 are led into and soldered within the sockets 71 in the rear terminal 66 (FIG. 4) so as to connect the three stator winding leads to three corresponding rear extending pins 46 in the pin holder 42. The insulated wires 77 are shown only fragmentarily in the drawings to avoid unduly cluttering the drawings. In FIGS. 1, 2 and 3 it will be seen that the insulated wires 77 and their corresponding notches 81 and 82 are on the far side of those figures and thereby are at least partially obscured.

The front and rear PC board disks 60 and 61 each comprise a conventional rigid insulative substrate, on the front and back sides of which are conventionally provided conductive foils generally indicated at 83 and provided in special patterns to effect the desired connections as hereafter discussed. To avoid unnecessarily cluttering the other drawings, the foils 83 are shown only in FIGS. 7 and 8.

The front PC board disk 60 has radially inboard and outboard arrays of circumferentially spaced conductive sockets 85 and 86 respectively, as seen in FIGS. 4 and 7. The outboard sockets 86 are arranged in widely circumferentially spaced groups of three closely circumferentially spaced sockets 86 each, with the circumferential spacing of the groups being substantially equal (i.e. at about 120° circumferential spacing). The inboard sockets 85 are evenly circumferentially spaced close around the bore 63. The conductive sockets 85 and 86 extend through the PC board 60. A ground socket 87 is circumferentially spaced between two of the triplets of sockets 86, close to the perimeter of the disk 60. The foils 83 of disk 60 conductively connect the conductive sockets 85 and 86 in the pattern shown in FIG. 7. The foils 83 on the front of the board 60 are shown in solid line and the foils 83 on the rear face of the board 60 are shown in dotted line.

Radially inboard and outboard circumferential arrays of conductive sockets 90 and 91 respectively are concentrically arranged on the rear PC board disk 61. The conductive sockets 90 and 91 extend through the disk 61. In the embodiment shown, the sockets 90 and 91 are preferably evenly circumferentially spaced within their respective arrays. A further conductive socket 92 is provided through the board 61 in the array of outboard sockets 91 and adjacent to one side of the notch 82. For purposes appearing hereafter, the sockets 90 and 91 are conductively connected by the pattern of foils 83 shown in FIG. 8. The foils 83 on the front of the board 61 are shown in solid line and the foils 83 on the back of the board 61 are shown in dotted line.

Figure 8:
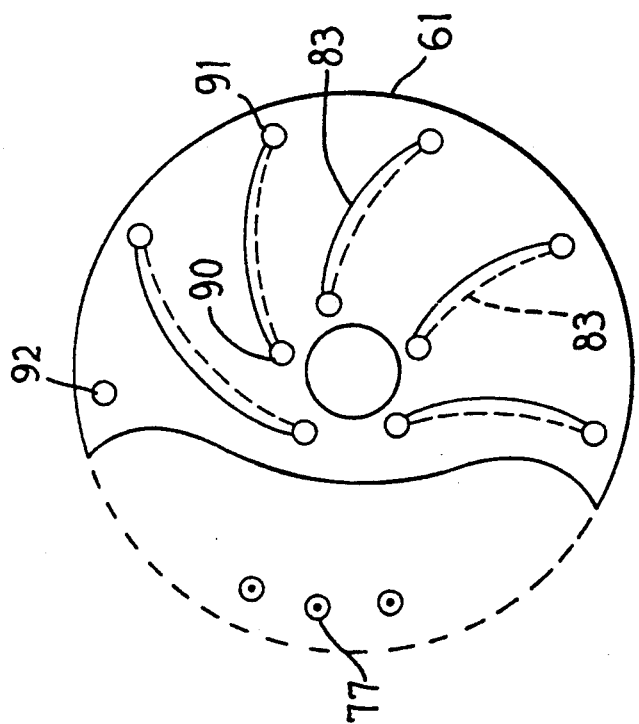
FIG. 8 is an enlarged front elevational view of a rear printed circuit board disk of FIG. 4.

The forward extending pins 70 of the five terminals 65 (FIG. 4) extend forward from the bottom wall 43 of the pin holder 42 and are received in axially aligned ones of the radially outer circumferential array of conductive sockets 91 in the rear PC board disk 61 to thereby fixedly locate the rear PC board disk 61 in close spaced relation ahead of the pin holder 42, as seen in FIGS. 2 and 3, and to electrically connect the pins 70 to corresponding ones of the conductive sockets 90 of the radially inner circumferential array as shown in FIG. 8. The pins 70 preferably extend through the thickness of the disk 61 so as to establish electrical connection with foils on both sides of the disk 61.

A further set of elongated conductive terminals 93 corresponds in number to the number of terminals 65. The elongated conductive terminals 93 each have an enlarged diameter midportion 94 from which extends forwardly a slim pin 95 and from which extends rearwardly a further slim pin 96. The terminals 93 are each, like the terminals 65, 66 and 67, continuously electrically conductive from end to end. In the embodiment shown, the terminals 93 are smaller in diameter than the terminals 65, 66 and 67 to better enable them to be circumferentially spaced while their front and rear pins 95 and 96 are plugged into respective axially aligned inboard conductive sockets 85 and 90 of the disks 60 and 61, respectively.

The terminals 93 thus respectively mechanically and electrically connect coaxially aligned ones of the conductive sockets 85 and 90 of the disks 60 and 61, respectively. More particularly, the terminals 93 have their rear pins 96 inserted into and electrically contacting corresponding conductive sockets 90 of disk 61 and have the pins 95 inserted into and electrically contacting corresponding conductive sockets 85 of disk 60. The mechanical contact of the pins 70, 96 and 95 with the respective sockets 91, 90 and 85 is a sufficiently snug and rigid friction fit as to positively fixedly locate the disks 60 and 61 coaxially in front of the pin holder 42. The connections of the pins 70, 96 and 95 with the electrically conductive sockets 91, 90 and 85, respectively, are soldered, to avoid loss of electrical contact due to corrosion after long use in a damp atmosphere.

Sensors 100, here three in number, each have a head 101. The heads 101 are circumferentially distributed about the rear end portion of the stator windings 31 (FIGS. 1 and 2) just behind the lamination stack 34. The sensor heads 101 sense the instantaneous angular position of the permanent magnet rotor 23 despite interposition of the stator windings 31 between the heads 101 and permanent magnet rotor 23. This is possible because the magnetic field of the permanent magnet rotor 23 is much stronger than the induced magnetic field of the stator windings 31 during motor operation.

The sensors 100 each further comprise three elongate, parallel, rearward extending, substantially rigid electrodes 102 (FIGS. 1-4). In the preferred embodiment shown, the sensors 100 are conventional Hall effect transistors, each having respective power supply input, ground, and open collector output electrodes 102.

Applicant has found that in order to achieve even (approximately 120°) circumferential spacing of the sensors 100, that one of these, namely the one indicated at 100A in FIG. 4, must be rotated 180° about its own length axis. More particularly, as seen in FIG. 4, the narrow face 103 of the sensor 100A faces radially inward, whereas the corresponding narrow faces 103 of the other two sensors 100 face radially outward. If all the sensors had their narrow face facing radially outward, the sensors 100 would all have to be located in unduly close packed circumferential relation which would cause a severe circumferential and radial crowding problem within the sensor-containing portion of the motor.

With the even circumferential spacing of the sensors 100 achieved by the reversal and orientation of one sensor 100A, the triplet of electrodes 102 of the three sensors 100 are circumferentially arranged to have their rear ends mechanically and electrically fixed in respective triplets of the outboard sockets 86 of the front PC board disk 60 (FIGS. 3 and 4). The particular sensors 100 shown have rigid, square cross section electrodes 102 of approximately 0.015 inch thickness, sufficient to reliably and rigidly support the heads 101 in forward cantilevered relation from the front PC board 60.

The rear bearing support 16 is provided with three evenly circumferentially spaced, generally L-shaped openings 110 (FIGS. 1-4 and 6). These L-shaped openings each include a portion extending radially inward along the bottom wall 27 and a portion extending rearward therefrom into the side wall 36. One of these openings 110, namely the one indicated at 110A, is included in the larger combination opening 80 and notch 81 above described. The three L-shaped openings 110 loosely receive rearwardly therethrough the electrodes 102 of corresponding ones of the sensors 100, to permit such electrodes 102 to pass rearwardly into the rear bearing support 16 and thereby into contact with the disk 60 contained within the rear bearing support. Forward of the disk 60, the electrodes 102 preferably are electrically insulated, as by covering with electrically insulative shrink fit tubing (not shown).

The pattern of foils 86 on the front PC board disk 60, seen in FIG. 7, effect the desired electrical connections from the sensor electrodes 102 to the terminals 93, and thus through the foils of the rear PC board 61 and the rear terminals 65, to the corresponding rear extending pins 46 of the pin holder 42. The foil pattern on the disk 60, as seen in FIG. 7, commonly connects the emitter electrodes 102 of the three sensors 100 to thereby permit connection thereof to ground as schematically indicated at 104 in FIG. 7, namely through the male connector "M" and remote motor control "R" of FIG. 1. Further, the foil pattern on the disk 60, as shown in FIG. 7, commonly connects the power supply input electrodes 102 of the three sensors 100 to a positive voltage supply 105 schematically shown in FIG. 1, namely through the male connector "M" and remote motor control "R" of FIG. 1. The remaining electrode 102 of each sensor 100, namely the open collector output thereof, constitutes the output electrode, on which the sensed signal appears, which sensed signal indicates the rotative position of the rotor 23. As seen in FIG. 7, the disk 60 has its foil pattern arranged so that each of the three sensor open collector outputs is separately connected (at 106, 107 and 108) through the male connector "M" to the remote motor control "R" of FIG. 1. It will, of course, be understood that all of these connections are effected through the foil connections of the front PC board 60, respective terminals 93, respective foil connections on rear PC board 61 and respective terminals 65 to respective pins 46 of the pin holder 42.

The elongated front pin 76 of the ground terminal 67 extends forward through the ground sockets 92 and 87 in the disks 61 and 60 respectively, thence into a hole 111 (FIGS. 2, 3 and 6) in the bottom wall 27 of the rear bearing support 16. The rear bearing support 16 is of conductive metal. Accordingly, the ground terminal 67 provides for electrical grounding of the rotor 23 through the male connector "M" to the remote motor control "R" of FIG. 1 in a conventional manner. This also grounds the motor housing in case of a winding short.

In addition, the ground terminal 67 mechanically helps to maintain correct circumferential orientation of the disks 60 and 61 with respect to the pin holder 42 and the rear bearing support 16.

To maintain rigid the positional relationships between the sensors 100, disks 60 and 61 and rear bearing support 16, the interior of the rear bearing support, behind the bottom wall 27 and ahead of the pin holder 42, is preferably flooded with a conventional potting compound of dielectric material, which is allowed to harden prior to assembly of the motor.

The motor is assembled preferably in the following manner.

The pin holder 42 has the terminals 65, 66 and 67 (FIG. 4) fixedly assembled thereon in their positions of FIGS. 2, 3 and 5.

The rear pins 96 of the terminals 93 are soldered in the inboard sockets 90 of the rear disk 61 to extend forward therefrom. The front pins 70 and 76 of the terminals 65 and 67 are soldered in the outboard sockets 91 and 92, respectively, of the rear disk 61. The rearward extending electrodes 102 of the Hall sensors 100 are soldered in the outboard triplet sockets 86 of the front disk 60. The pins 95 and 76 are respectively soldered in the inboard sockets 85 and outboard grounding socket 87 of the front disk 60. The resulting solder connections hold the PC boards 60 and 61 in spaced relation from each other and from the pin holder 42. The result is a pin holder-sensor subassembly 112 shown complete in FIG. 3 and exploded in FIG. 4.

Thereafter, the actuator buttons 47 are inserted into their holes 50 in the pin holder 42 and the O-ring 53, cam ring 51 and O-ring 45 are telescoped rearwardly over the subassembly 112 and more specifically over the pin holder 42. The rear bearing support 16 is then telescoped rearward over the subassembly 112, with the heads 101 of the Hall sensors 100 passing loosely forward through the respective openings 110. The screw 54 is inserted forward through the central opening in the bottom wall 43 of the pin holder 42, loosely through the central bores 63 and 64 of the disks 60 and 61, to then thread centrally into the bottom 27 of the rear bearing support 16 tightening the screw snugly abuts the bottom wall 43 of the pin holder 42 against the step 41 and the rear bearing support 16. In this position, the front disk 60 is spaced behind the bottom 27 of the rear bearing support 16 so as to avoid any contact of the latter with the foils 83 on the front of the disk 60. The front end of the ground pin 76 is then soldered in the corresponding hole 111 in the bottom 27 of the metal (preferably stainless steel) rear bearing support 16.

It is convenient to continue assembly with the rotation axis of the motor upright, with the rear end of the pin holder 42 sitting on a suitable work surface and the neck 18 extending upward therefrom. The spring 26 and washer 28 can then be dropped into the interior of the neck, to rest on the rear bearing support bottom 27.

A stator subassembly 113 is defined by the assembled dielectric sleeve 30, stator windings 31, outer dielectric sleeve 32 and lamination stack 34, rigidly bonded together. The rear end of the stator subassembly 113 is telescoped over the neck 18. The three stator end wires 77 from the rear end of the stator windings 31 are led through the opening, notch 80,81 in the rear bearing support 16. The wires 77 extend rearward past the notch 82 in the rear disk 61 and have bared rear ends received in the sockets 71. The notch 81 in the rear bearing housing 16 and the notch 82 in the periphery of the rear disk 61 provide room enough for soldering the bared rear ends of the wires 77 in respective ones of the sockets 71.

A rotor assembly 114 is defined by the permanent magnet rotor 23, with the front and rear bearings 21 and 22 fixed on its front and rear shaft ends 24 and 25, respectively with the spring 26 and washer 28 already in the neck 18, the rotor assembly 114 is inserted rearward into the inner dielectric sleeve 30 of the stator subassembly 113 until the rear bearing 22 is snugly but slidably received in the neck 18 atop the washer 28 and spring 26. The front bearing support 15 is then inserted into the front end of the stator assembly 113.

To assure precisely correct circumferential orientation of the stator windings 31 with respect to the Hall sensors 100, the motor is electrically energized to run (for example, by means of the male connector "M" and the remote motor control "R") while the stator assembly is circumferentially adjusted with respect to the rear bearing support and hence with respect to the Hall sensors 100. Such energization is stopped when the stator assembly is properly angularly oriented with respect to the sensors 100.

The rotor assembly 114 and front bearing support 15 are then temporarily removed. Keeping the angular position of the stator assembly 113 with respect to the Hall sensors 100, the stator assembly 113 is slid forward partway along the neck 18 (the wires 77 having sufficient slack to allow this forward movement) and an adhesive is placed on the exposed portion of the neck. Thereafter the stator assembly 113 is slid rearward to its desired position shown in FIG. 1, wherein a portion of the inner dielectric sleeve 30 of the stator assembly 113 overlies the adhesive and is bonded thereby to the neck 18 in a fixed manner.

Thereupon completion of assembly of the apparatus proceeds by again inserting the rotor assembly 114 to locate the rear bearing 22 within the neck 18 and the permanent magnet rotor 23 within the stator assembly. The front bearing support 15 at this point is no longer sleeved over the front end of the rotor assembly 114.

Still with the rotational axis of the motor vertical, the rear bearing support 16 can be temporarily surrounded with masking tape to cover the rear extending portions of the L-shaped openings 110. Thereafter, a flowable conventional potting compound can be poured into the rear bearing support, to flow into the space axially between the rear bearing support bottom 27 and the bottom wall 43 of the pin holder 42 and thereby fixedly hold the contents thereof in place in a rigid manner. Once the potting compound is hardened, the masking tape can be removed and the apparatus is ready for installation in the outer housing 11. The rotor is usually removed before pressing the housing on to prevent damage to the rotor.

The housing 11 is slid rearward over the stator assembly 113 and the rear bearing support 16, to abut the flange 40 of the rear bearing support 16. The rotor is then inserted rearward into the housing 11 so its rear bearing 22 is reset in the neck 18. The front bearing support 15 can then be inserted rearward into the front end of the housing 11, the rear end of the front bearing support 15 being received snugly over the front bearing 21 to support same for rotation of the permanent magnet rotor 23 and being received snugly within the front end of the stator assembly 113 to help fixedly support that with respect to the rotor assembly 114.

Thereafter, a conventional chuck C may be fixed on the front shaft end 24 to receive various surgical tools T. With the connection of the male connector M to the rear end of the pin holder 42 and with energization of the remote motor control R connected thereto, the resulting surgical handpiece is ready to operate.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. A dc permanent magnet motor for a surgical handpiece, comprising:
   a housing;
   a stator including windings fixed in said housing;
   a rotor supported for rotation in said housing and having a forward extending rotatable shaft;

a conventional sensor adjacent said windings and rotor and having stiff conductive electrodes extending rearward;

a printed circuit board disk having plural axial holes along the perimeter thereof defining conductive sockets into which said electrodes plug and located coaxially rearward of said rotor and windings and fixed with respect to said housing;

a rear facing, separable connector holder behind said printed circuit board and having first terminals rear facing therefrom for connection to an external electrical supply, said holder being fixed with respect to said housing;

means electrically connecting said conductive sockets of said printed circuit board to said rear facing terminals of said holder.

2. The apparatus of claim 1 including a rear bearing for rotatably supporting said shaft and a rear bearing support supporting said rear bearing coaxially of said shaft and housing, said rear bearing support comprising a rear body fixedly telescoped in the rear end of said housing and a reduced diameter front neck of diameter less than that of said rear body and coaxially fixed with respect to said rear body by a step, said rear bearing being coaxially fixed in said reduced diameter front neck.

3. The apparatus of claim 2 means defining an aperture in said step, said sensor electrodes extending rearward outside said front shell and loosely through said aperture, said printed circuit board being in said rear shell.

4. The apparatus of claim 1 in which said electrically connecting means includes a second printed circuit board in said rear body between said first printed circuit board and said holder, and a circumferential array of conductive, elongate rod-like terminals interconnecting said first and second printed circuit boards, the radius of the last-mentioned circumferential array being substantially less than the radius from the motor axis out to said sensor electrodes and said sockets receiving said sensor electrodes in said first printed circuit board.

5. The apparatus of claim 4 in which said electrically connecting means comprises a circumferential array of axially elongate electrical conductors extending forward from said terminals of said holder to said second printed circuit board, said second-mentioned array being spaced on said second printed board radially outside said first-mentioned array.

6. The apparatus of claim 5 including means rotatably supporting the rear end of said shaft and an elongate screw coaxially extending forward through said holder and second printed circuit board and first printed circuit board and into said means supporting the rear end of said shaft to fixedly locate these four elements with respect to said housing.

7. The apparatus of claim 6 in which said means supporting the rear end of said shaft comprises a rear bearing support supporting said rear bearing coaxially of said shaft and housing, said rear bearing support comprising a rear body fixedly telescoped in the rear end of said housing and a reduced diameter front neck of diameter less than that of the rear body and coaxially fixed with respect to said rear body by a step, said rear bearing being coaxially fixed within said reduced diameter front neck.

8. The apparatus of claim 4 including means in said housing supporting said rotor for rotation, elongate wires connecting said windings to ones of said rear facing terminals of said holder and extending forward past said printed circuit boards to said means for supporting said rotor for rotation, said holder having a forward facing step and an aperture in said step through which said wires extend, one of said printed circuit boards having a notch in its periphery for running of said wires therepast.

9. The apparatus of claim 4 including means fixed with respect to said housing for rotatably supporting said rotor, a rod-like elongate conductive ground element defining one of said terminals extending rearward from said holder, said ground element extending forward through holes in said first and second printed circuit boards and into conductive and rigid mechanical connection with said means supporting said rotor.

10. The apparatus of claim 1 including plural ones of said sensors circumferentially spaced about the motor axis, said sensors having respective sets of electrodes arranged in a circumferential array and extending rearward into respective ones of said plural axial conductive sockets distributed circumferentially along the perimeter portion of said printed circuit board disk.

11. The apparatus of claim 10 in which said sensors are Hall effect transistors each having a body with a reference face, said sensors being spaced at about 120° circumferential spacing around said rotor, all said sensors having their reference faces facing away from said rotor except for one, which one has its reference face facing toward said rotor.

12. The apparatus of claim 2 in which said rear body inserts snugly and sealing into the rear of said housing, said holder inserts into said rear body and an annular seal member is disposed between said holder and rear shell to prevent fluid leakage forward into said housing.

13. The apparatus of claim 12 in which said holder has front facing conductors sealed therein for preventing fluid leakage along said conductors into said housing, said conductors being forward extensions of said first terminals.

14. The apparatus of claim 12 including a screw extending forward coaxially through said holder and printed circuit board and threaded into a portion of said rear bearing support forward of said printed circuit board to axially compressively connect same, said screw being in sealing engagement with said holder to block leakage into said housing therealong.

15. A permanent magnet dc motor for a surgical handpiece, comprising:

a housing;

a stator including windings fixed in said housing;

a rotor supported for rotation in said housing and having a forward extending rotatable shaft;

a plurality of conventional sensors adjacent said windings and rotor, said sensors each having stiff conductive electrodes extending rearward therefrom, said electrodes being arranged in a circumferential array around the axis of said rotor;

front and rear coaxial, disk-like printed circuit boards, said front board having a circumferentially spaced array of conductive sockets adjacent the perimeter thereof into which the rear ends of respective ones of said electrodes insert;

first circumferentially spaced, conductive pins in an array spaced radially in from said conductive sockets array in said front board, said first conductive pins extending between and connecting said printed circuit boards;

a rear facing, separable connector holder behind said printed circuit boards and having rear facing conductors for connection to an external electrical supply, said holder being fixed with respect to said housing;

second circumferentially spaced conductive pins in an array spaced radially out from said first pins array, said second pins array connecting said rear board to said holder;

means on said front board for electrically connecting ones of said sockets to respective pins of said first pins array in a desired pattern;

means on said rear printed circuit board for electrically connecting ones of said conductive pins of said first array to selected ones of said pins of said second pins array in a desired pattern;

means effecting connection of said second pins to said rear facing conductors on said holder.

* * * * *